US008975284B2

(12) United States Patent
Malkawi et al.

(10) Patent No.: US 8,975,284 B2
(45) Date of Patent: Mar. 10, 2015

(54) CO-SOLVENT COMPOSITIONS AND METHODS FOR IMPROVED DELIVERY OF DANTROLENE THERAPEUTIC AGENTS

(75) Inventors: Ahmad Malkawi, Lexington, KY (US); Abeer M. Al-Ghananeem, Lexington, KY (US); Patrick DeLuca, Lexington, KY (US); George A. Digenis, Louisville, KY (US)

(73) Assignee: US WorldMeds LLC, Louisville, KY (US)

( * ) Notice: Subject to any disclaimer, the term of this patent is extended or adjusted under 35 U.S.C. 154(b) by 1113 days.

(21) Appl. No.: 12/205,303

(22) Filed: Sep. 5, 2008

(65) Prior Publication Data

US 2009/0093531 A1 Apr. 9, 2009
US 2011/0015243 A2 Jan. 20, 2011
US 2011/0160261 A2 Jun. 30, 2011

Related U.S. Application Data

(60) Provisional application No. 60/978,626, filed on Oct. 9, 2007.

(51) Int. Cl.

| A01N 43/40 | (2006.01) |
| A61K 31/44 | (2006.01) |
| A01N 43/50 | (2006.01) |
| A61K 31/415 | (2006.01) |
| A01N 43/00 | (2006.01) |
| A61K 31/33 | (2006.01) |
| A61K 9/00 | (2006.01) |
| A61K 9/08 | (2006.01) |
| A61K 9/19 | (2006.01) |
| A61K 31/4166 | (2006.01) |
| A61K 31/4168 | (2006.01) |

(52) U.S. Cl.
CPC ............... *A61K 9/0019* (2013.01); *A61K 9/08* (2013.01); *A61K 9/19* (2013.01); *A61K 31/4166* (2013.01); *A61K 31/4168* (2013.01)
USPC ........................... 514/341; 514/389; 514/183

(58) Field of Classification Search
None
See application file for complete search history.

(56) References Cited

U.S. PATENT DOCUMENTS

| 3,415,821 A | 12/1968 | Davis et al. |
| 4,543,359 A | 9/1985 | Ellis et al. |
| 5,122,110 A | 6/1992 | McNally et al. |
| 5,145,769 A | 9/1992 | McNally et al. |
| 5,149,621 A | 9/1992 | McNally et al. |
| 5,158,867 A | 10/1992 | McNally et al. |
| 5,506,231 A | 4/1996 | Lipton |
| 5,597,809 A | 1/1997 | Dreyer |
| 8,436,190 B2 | 5/2013 | Brittain et al. |
| 8,445,524 B2 | 5/2013 | Courvoisier et al. |
| 8,461,350 B2 | 6/2013 | Brittain et al. |
| 8,609,863 B2 | 12/2013 | Brittain et al. |
| 8,669,279 B2 | 3/2014 | Cooper et al. |
| 8,791,270 B2 | 7/2014 | Brittain et al. |
| 2004/0242646 A1* | 12/2004 | Anderson et al. .............. 514/341 |
| 2006/0159713 A1 | 7/2006 | Brittain et al. |
| 2007/0116729 A1* | 5/2007 | Palepu .......................... 424/400 |
| 2013/0131131 A1 | 5/2013 | Brittain et al. |
| 2014/0148490 A1 | 5/2014 | Brittain et al. |
| 2014/0187598 A1 | 7/2014 | Cooper et al. |

FOREIGN PATENT DOCUMENTS

| EP | 0 757 910 | 2/1997 |
| JP | 6263636 | * 9/1994 |
| WO | WO 03/000057 | 1/2003 |

OTHER PUBLICATIONS

Kiyoshi (English translation of JP6263636, cited by Applicant in the IDS filed Apr. 9, 2009).*
Teagarden and Baker, Practical aspects of lyophilization using non-aqueous co-colvent systems, 2002, European Jounal of Pharmaceutical Sciences, 15, pp. 115-133.*
International Preliminary Report on Patentability dated Apr. 13, 2010 for Application No. PCT/US2008/075406.
International Search report dated Feb. 26, 2009 for Applicaton No. PCT/US2008/075406.
Jansen, A.C.A. et al., "Some physical—chemical properties of dantrolene and two of its analogues," International Journal of Pharmaceutics, vol. 75 (Sep. 20, 1991) pp. 193-199.
Krause, T. et al., "Dantrolene—A review of its pharmacology, therapeutic use and new developments," Anaesthesia, vol. 59 (2004) pp. 364-373.
Office Action dated 09/27/2010 for Application No. EP 08 837 079.
Snyder, H.R. et al., "1-[(5-Arylfurfurylidene)amino]hydantoins. A new class of muscle relaxants," Journal of Medicinal chemistry, vol. 10 (1967) pp. 807-809.
Abrstract of Salata et al., "Effects of Dantrolene Sodium on the Electrophysiological Properties of Canine Cardiac Purkinje Fibers," J. Pharmacol. Exp. Ther., vol. 220(1) (Jan. 1982). pp. 157-166.
Abstract of Teagarden, D,L. et al., "Practical Aspects of Lyphilization using Non-Aleuous Co-Solvent Systems," Dept. of Sterile Products Development, Pharmacia Corp, Eur J Pharm Sci, vol. 15, Iss 2, Mar. 2002.
Friesen et al., Can. Anaesth. Soc. J., vol. 26 (1979) pp. 319-321.

(Continued)

*Primary Examiner* — Jeffrey S. Lundgren
*Assistant Examiner* — Tori M Strong
(74) *Attorney, Agent, or Firm* — Frost Brown Todd LLC

(57) ABSTRACT

The present invention provides for methods of using tert-butyl alcohol (TBA) co-solvent systems in the formulation and production of a pharmaceutical agent with low solubility. The present invention also provides for pharmaceutical compositions made using the novel co-solvent system. In one embodiment, the invention provides for a method of making dantrolene sodium (DS) formulation for intravenous use (DS-IV). This instantaneous reconstitution of the DS-IV product constitutes a significant improvement in the pharmacotherapy of patients undergoing malignant hyperthermia during surgery.

19 Claims, 1 Drawing Sheet

(56) References Cited

OTHER PUBLICATIONS

International Conferences on Harmonization, Impurities-Guidelines for Residual Solvents, Q3C Federal Register 62(247):67377 (1997).

Kasraian, K. et al., "The effect of tertiary butyl alcohol on the resistance of the dry product layer during primary drying," Pharmaceutical Research, vol. 12(4) (1995) pp. 491-495.

Kasraian, K. et al., "Thermal analysis of the tertiary butyl alcohol-water system and its implications on freeze-drying," Pharmaceutical Research, vol. 12(4) (1995) pp. 484-490.

Wittaya-Areekul, S. et al., "Freeze-drying of tertiary butanol/water co-solvent systems: a case report on formation of friable freeze-dried powder of tobramycine sulfate," J. Pharmaceutical Sciences, vol. 91(4) (2002) pp. 1147-1155.

European Patent Office, Third Party Observations according to Article 115 and Rule114 EPC dated Apr. 23, 2013 for Application/Publication No. 08837079.6/EP 2219605-A1.

European Patent Office, Third Party Observations according to Article 115 and Rule114 EPC dated May 16, 2013for Application/Publication No. 08837079.6/EP 2219605-A1.

European Patent Office, Third Party Observations according to Article 115 and Rule114 : EPC dated Jan. 16, 2014 for Application/Publication No. 08837079.6/EP 2219605-A1.

European Office Action dated Mar. 4, 2014 for Application No. EP 08837079.6.

Dirk L. Teagarden, David S. Baker, Practical aspects of lyophilization using non-aqueous co-solvent systems, European Journal of Pharmaceutical Sciences 15 (2002), 115-133.

European Communication, Third Party Observations, dated Sep. 18, 2014 for Application No. 12187466.3.

\* cited by examiner

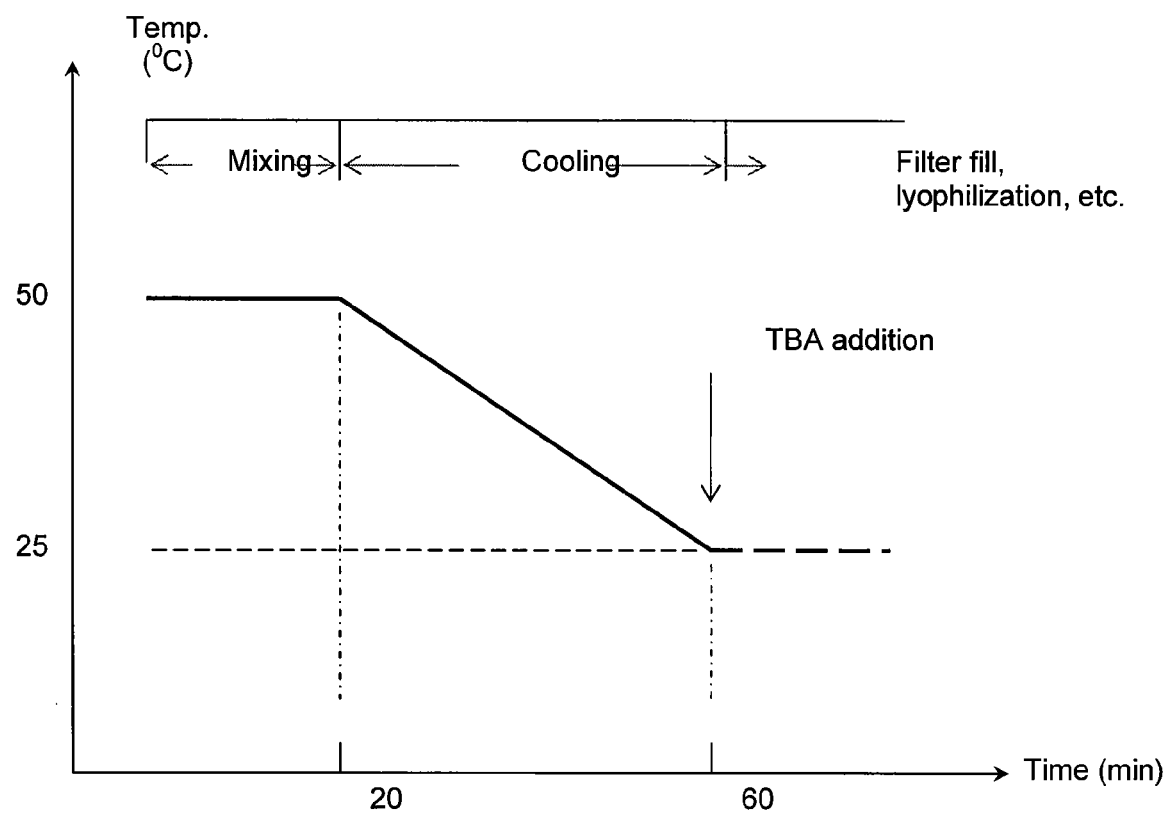

CO-SOLVENT COMPOSITIONS AND METHODS FOR IMPROVED DELIVERY OF DANTROLENE THERAPEUTIC AGENTS

CROSS-REFERENCE TO RELATED APPLICATIONS

This application claims priority to U.S. Provisional Patent Application Ser. No. 60/978,626, which was filed on Oct. 9, 2007, the entirety of which is incorporated herein by reference for all purposes.

FIELD OF THE INVENTION

The present invention relates generally to a co-solvent system for formulation and production of a pharmaceutical agent with increased solubility. The present invention also provides for methods of using tert-butyl alcohol (TBA) co-solvent systems in the formulation and production of a pharmaceutical agent with low solubility. The present invention also provides for pharmaceutical compositions made using the novel co-solvent system. In one embodiment, the invention provides for a method of making a dantrolene formulation for intravenous use. The resulting product has the ability of rapid reconstitution of the dantrolene product, which constitutes a significant improvement in the pharmacotherapy of patients undergoing malignant hyperthermia during surgery.

BACKGROUND OF THE INVENTION

Dantrolene sodium (1-[[5-(p-nitrophenyl)furfurylidene]-amino]hydantoin sodium salt) is described in U.S. Pat. No. 3,415,821, incorporated herein by reference in its entirety. It can be used as a skeletal muscle relaxant particularly in controlling the manifestations of clinical spasticity resulting from upper neuron disorders (Physicians' Desk Reference, 36th Edition, 1982). It is also used in the prevention and treatment of malignant hyperthermia in humans (Friesen et al., Can. Anaesth. Soc. J. 26:319-321, 1979).

In connection with the use of dantrolene sodium in hyperthermic crisis it was observed that there was an elimination of the arrhythmias accompanying such crisis [Salata et al., Effects of Dantrolene Sodium on the Electrophysiological Properties of Canine Cardiac Purkinje Fibers, J. Pharmacol. Exp. Ther. 220(1): 157-166 (January) 1982], incorporated herein by reference in its entirety. Dantrolene sodium is useful as a cardiac antiarrhythmic agent in hypothermic and normothermic warm-blooded animals as described in U.S. Pat. No. 4,543,359, incorporated herein by reference in its entirety.

It is also known that dantrolene sodium prevents or reduces arrhythmia in hypothermic and normothermic warm-blooded animals. In particular, dantrolene sodium is effective in the treatment of supraventricular tachycardias, in suppressing slow responses in infarcted tissues and in abolishing ventricular premature beats or tachycardias originating in these tissues, and in correcting ventricular rhythm disturbances due to reentry.

Malignant hyperthermia had a mortality rate of nearly 80 percent at the time it was identified in 1960. Treatment consisted only of cooling the patient and treating the specific symptoms, but not the underlying cause. Since 1979, the antidote drug dantrolene sodium has been available for the treatment of malignant hyperthermia and has contributed greatly to a dramatic decline in mortality. The syndrome must be identified and treated early for a successful outcome.

Dantrolene sodium for injection comes as a dry powder that must be dissolved in sterile water prior to injection. Generally, it is supplied in small glass containers containing enough powder to give about 16 to about 20 mg of the active drug.

Although most cases of malignant hyperthermia respond to 2.5-4.0 mg/kg of dantrolene initially, some patients need significantly more to bring the episode under control. In addition, recrudescence is a possibility within the first few days of treatment. Finally, because of the need for continued treatment for at least 48 hours after malignant hyperthermia at a dose of about 1 mg/kg every 4 hours, the Malignant Hyperthermia Association of the United States (MHAUS) recommends that 36 vials be stocked.

The active pharmaceutical ingredient (API) (DS) undergoes slow hydrolytic decomposition in aqueous media. This degradation is accelerated at higher (alkaline) pH values and is enhanced by elevated temperatures. Thus, these conditions should be avoided as much as possible during the production of the final product (DS-IV).

The insolubility of DS in water necessitates its dissolution at a considerably higher pH than its pKa value. The higher pH of its formulation requirement results in: a) the alkaline hydrolysis (loss of potency) of DS, and b) susceptibility of its solution to carbon dioxide during its introduction into vials (filling of vials). The atmospheric carbon dioxide ($CO_2$) appears to interact with the alkaline (e.g., NaOH) content of the filled vials resulting in the reduction of the pH of their solution resulting in a possible undesirable effect in the DS formulation. Thus, the above two phenomena require that the dissolution of the DS (API) at the time of its formulation process and the subsequent introduction of its solution to vials be expedited prior to the commencement of its freeze-drying.

There is a significant need in the art for a satisfactory formulation of dantrolene sodium with greater solubility in a formulation that remains stable enough for practical use.

The present invention teaches the use of a novel organic solvent/water co-solvent system that reduces (a) freezing time of the DS-IV formulation, (b) its freeze-drying time and (c) the reconstitution time of the DS freeze-dried product. A faster reconstitution of the DS-IV product provides a great pharmacotherapeutic advantage in the treatment of patients exhibiting the life-threatening condition of malignant hyperthermia (MH) while undergoing surgery. On average, these patients generally require a rapid intravenous (IV) infusion of nine to ten (9-10) vials of DS-IV product, generally comprising from about 2.5 to about 10 mg/kg patient weight, and each reconstituted with about 60 mL of sterile water for injection (WFI) (See, for example, Merck Manual, 18th Edition, 2006). In many cases, the number of DS-IV vials used ranges from about 10 to about 20 but can be even more. Cases of MH requiring as many as 36 vials of DS-IV have been recorded. The length of time to reconstitute the necessary 10-36 vials (at approximately 1 to 3 min each) creates a significant issue when considering MH death can occur in as short time as 30 min from onset.

Organic co-solvent systems encompass a wide variety of organic solvents (examples: tert butyl alcohol, ethanol, n-propanol, n-butanol, iso-propanol, ethyl acetate, acetone, methyl acetate, methanol, carbon tetrachloride, dimethylsulfoxide, chlorobutanol, cyclohexane, and acetic acid).

The formulation of Caverject™ (Alprostadil) (Pfizer) is an example of sterile marketed injectable product that has been freeze-dried from a TBA-water solution. Table 1 lists several examples of freeze-dried preparations using co-solvent systems.

TABLE 1

Examples of compounds freeze-dried with co-solvent system.

| Drug | Co-solvent System | Reference |
| --- | --- | --- |
| Alprostadil (CAVERJECT ® S.Po.) | 20% v/v tert-butanol/water | Teagarden et al., 1998a |
| Aplidine | 40% v/v tert-butanol/water | Nuijen et al., 2000 |
| Amoxicillin sodium | 20% v/v tert-butanol/water | Tico Grau et al., 1988 |
| Gentamicin sulfate | tert-Butanol/water | Baldi et al., 1994 |
| N-Cyclodexyl-N-methyl-4-(2-oxo-1,2,3,5-tetrahydroimidazo-[2.1-b]quinazolin-7-yl)oxybutyratnide with ascorbic acid | 50% v/v tert-butanol/water | Benjamin and Visor, 1989 |
| Cyclohexane 1.2-diamine Pi(II) complex | tert-Butanol | Tanno et al., 1990 |
| Fructose-1.6-diphosphate | tert-Butanol/water | Sullivan and Marangos, 1998 |
| Annamycin | tert-Butanol/dimethyl sulfixide/water | Zou et al., 1999 |
| Cephalothin sodium | 5% w/w isopropyl alcohol/water | Koyama et al., 1988 |
| Cephalothin sodium | 4% ethanol, 4% methanol or 4% acetone/water | Cise and Roy, 1981 |
| Prednisolone acetate/polyglycolic acid | Carbon tetrachloride/ hexafluoroacetone sesquihydrate | DeLuca et al., 1989a |
| Gabexate mesylate | Ethanol/water | Kamijo et al., 1987 |
| Piraubidin hydrochloride | Ethanol/water | Kaneko et al., 1993 |
| Progesterone, coronene, fluasterone, phenytoin | Chlorobutanol hemihydrate/Dimethyl sulfone | Tesconi et al., 1999 |
| Poly (lactide-co-glycolide) | Acetic acid | Meredith et al., 1996 |
| Dioleoylphosphatidylcholine and dioleoylphophatidyl glycerol | Cyclohexane | Felgner and Eppstein, 1991 |
| Vecuroniumbromide | Acetonitrile | Jansen, 1997 |
| Bovine pancreatic trypsin inhibitor | Dimethyl sulfoxide/1% water | Desai and Klibanov, 1995 |

BRIEF SUMMARY OF THE INVENTION

The present invention relates generally to a co-solvent system for formulation and production of a pharmaceutical agent with increased solubility. This invention also relates generally to a method of freeze-drying a pharmaceutical formulation using a co-solvent system.

The present invention also provides for methods of using tert-butyl alcohol (TBA) co-solvent systems in the formulation and production of a pharmaceutical agent with low solubility. The present invention also provides for pharmaceutical compositions made using the novel co-solvent system.

In one embodiment, the invention provides for a method of making dantrolene sodium (DS) formulations for intravenous use (DS-IV). This substantially instantaneous reconstitution of the DS-IV product constitutes a significant improvement in the pharmacotherapy of patients undergoing malignant hyperthermia during surgery. In one embodiment, this substantially complete dissolution is accomplished in less than about 30 seconds. In one embodiment, this substantially complete dissolution is accomplished in about 10 to about 20 seconds.

In one embodiment, the present invention provides for the production of the DS-IV product involving three (3) major steps. These are as follows:
1. Formulation of the active pharmaceutical ingredient (API) dantrolene sodium at an alkaline pH.
2. Addition of a co-solvent to make the DS solution; and filling the vials containing the solution ("fill" solution) to be lyophilized.
3. A lyophilization cycle of the DS solution to produce the freeze-dried sterile DS-IV product.

The present invention is also directed to stable pharmaceutical compositions of dantrolene sodium, in particular lyophilized dantrolene sodium and its use in treatment of various disease states, especially neural diseases and malignant hyperthermia and other conditions involving high fever.

An embodiment of the invention is a pharmaceutical composition of dantrolene sodium comprising trace amounts of organic solvent after reconstitution of a lyophilized pharmaceutical composition of dantrolene sodium as described herein.

Another embodiment of the invention is a lyophilized preparation of dantrolene sodium comprising about 0.001% to about 0.3% dantrolene sodium after reconstitution. Another embodiment of the invention is a lyophilized preparation of dantrolene sodium comprising about 0.01% to about 0.1% dantrolene sodium after reconstitution. Yet another embodiment of the invention is a lyophilized preparation of dantrolene sodium comprising about 0.015% to about 0.05% dantrolene sodium after reconstitution.

In preferred aspects of the invention, the dosage form can be about 5 to about 50 mg of dantrolene sodium, about 10 to about 30 mg of dantrolene sodium, about 10 mg to about 20 mg of dantrolene sodium, and about 20 mg of dantrolene sodium.

Yet another embodiment of the invention is a pharmaceutical dosage form that includes a lyophilized preparation of dantrolene sodium containing not more than about 0.05% to about 1%, preferably 0.6% to about 0.7%, DS-IV (w/w). In certain embodiments, dosage forms can be about 5 to about 720 mg of dantrolene sodium, about 10 to about 300 mg of dantrolene sodium, about 10 to about 100 mg of dantrolene sodium, and about 12 mg to about 22 mg of dantrolene sodium.

In still another embodiment, the invention includes a pharmaceutical composition of dantrolene sodium including dantrolene sodium containing not more than about 5% of one or more organic solvents after reconstitution of a lyophilized pharmaceutical composition of dantrolene sodium as disclosed herein.

In different aspects of this embodiment, the organic solvent is selected from one or more of tertiary butanol, n-propanol, n-butanol, isopropanol, ethanol, methanol, acetone, ethyl acetate, dimethyl carbonate, acetonitrile, dichloromethane, methyl ethyl ketone, methyl isobutyl ketone, 1-pentanol, methyl acetate, carbon tetrachloride, dimethyl sulfoxide, hexafluoroacetone, chlorobutanol, dimethyl sulfone, acetic acid, and cyclohexane.

In one specific embodiment, the organic solvents include one or more of ethyl, methyl, propyl, butyl alcohol. In another embodiment, the organic solvent is tertiary butanol, also known as TBA, t-butanol, tert-butyl alcohol or tertiary butyl alcohol, alone or in combination with one or more additional solvents. In another embodiment, the organic solvent comprises at least 20, 30, 40, 50, 60, 70, 80, 90, 95, 98 99 or more percent (v/v) alcohol in combination with one or more additional solvents. In another embodiment, the organic solvent comprises at least 20, 30, 40, 50, 60, 70, 80, 90, 95, 98 99 or more percent (v/v) butanol in combination with one or more additional solvents. In another embodiment, the organic solvent comprises at least 30 percent (v/v) tertiary butanol in combination with one or more additional alcohols.

Another embodiment of the invention is a process for manufacturing a lyophilized preparation of dantrolene sodium which includes controlling the particle size of dantrolene sodium in the final product.

Another embodiment of the invention is a dantrolene sodium pre-lyophilization solution or dispersion comprising one or more organic solvents where the solution or dispersions include at least one stabilizing concentration of an organic solvent such that the dantrolene sodium product produced during lyophilization is capable of rapid reconstitution. In one embodiment, the dantrolene sodium product is cable of substantial reconstitution in a carrier in less than about 10, 8, 5, 4, 3, 2, or 1 minute(s). In another embodiment, the dantrolene sodium product is cable of substantial reconstitution in a carrier in less than about 30 seconds. In another embodiment, the dantrolene sodium product is cable of substantial reconstitution in a carrier in less than about 20 seconds. In another embodiment, the dantrolene sodium product is cable of substantial reconstitution in a carrier in about 10-20 seconds.

An aspect of this embodiment is the lyophilized powder produced from the pre-lyophilization solution or dispersion.

The invention also discloses methods for preparing a dantrolene sodium lyophilized preparation that includes dissolving dantrolene sodium in a stabilizing concentration of an alcohol solvent of between about 1% to about 99.9% (v/v alcohol to form a pre-lyophilization solution; and lyophilizing the pre-lyophilization solution; wherein the dantrolene sodium lyophilized preparation made from such methods comprises an excipient.

Other alcohol concentrations include about 1% to about 99%, about 1% to about 70%, about 2% to about 60%, about 3% to about 50%, about 2% to about 40%, about 2% to about 35%. Preferred concentrations of alcohol are from about 2% to about 30%.

In one embodiment, the alcohols include one or more of methanol, ethanol, propanol, iso-propanol, butanol, and tertiary-butanol. In another embodiment, the alcohol is tertiary-butanol (tertiary butyl alcohol or TBA). In another embodiment, the concentration of tertiary-butanol is about 0.5% to about 30%. In another embodiment, the concentration of tertiary-butanol is about 1% to about 20%. In another embodiment, the concentration of tertiary-butanol is about 2% to about 10%. An aspect of this embodiment is the addition of excipients before lyophilization. In one embodiment, excipients are mannitol, sodium hydroxide (NaOH) or mixtures thereof.

In one embodiment, the pre-lyophilized concentrations of dantrolene sodium are from about 0.1 mg/mL to about 50 mg/mL. In another embodiment, the pre-lyophilized concentrations of dantrolene sodium are from about 0.2 mg/mL to about 10 mg/mL. In another embodiment, the pre-lyophilized concentrations of dantrolene sodium are from about 0.2 mg/mL to about 5 mg/mL. In yet another embodiment, the pre-lyophilized concentrations of dantrolene sodium are from about 0.2 mg/mL to about 1 mg/mL.

In one embodiment of the invention, there is provided a method for preparing a dantrolene sodium lyophilized preparation comprising a) dissolving dantrolene sodium in a solution of water and organic co-solvent solution comprising between about 1% to about 99% (v/v) organic co-solvent to form a pre-lyophilization solution; and b) lyophilizing the pre-lyophilization solution.

In another embodiment, lyophilizing the pre-lyophilization solution comprises
i) cooling the pre-lyophilization solution to a temperature capable of forming a frozen solution;
ii) holding the frozen solution a temperature capable of forming a frozen solution, for a time sufficient to substantially freeze the solutions;
iii) ramping the frozen solution to a primary drying temperature;
iv) holding at a primary drying temperature at a temperature and for a time sufficient to form a substantially dried lyophilized product;
v) optionally ramping the dried solution to a secondary drying temperature; and
vi) optionally holding at the secondary drying temperature at a temperature and for a time sufficient to form a substantially dried dantrolene sodium lyophilized preparation.

In another embodiment of the invention, there is provided a stable and lyophilized formulation of dantrolene sodium made by the process comprising a) dissolving dantrolene sodium in a solution of water and organic co-solvent solution comprising between about 1% to about 99% (v/v) organic co-solvent to form a pre-lyophilization solution; and b) lyophilizing the pre-lyophilization solution.

In another embodiment, lyophilizing the pre-lyophilization solution comprises: i) freezing the pre-lyophilization solution to a temperature below about −20° C. for a time sufficient to substantially freeze the solution; ii) drying the frozen solution at a drying temperature between about −60° C. and about 30° C. to form a dantrolene sodium lyophilized preparation.

In another embodiment, lyophilizing the pre-lyophilization solution comprises: i) freezing the pre-lyophilization solution to a temperature below about −40° C. for a time sufficient to substantially freeze the solution; ii) drying the frozen solution at a drying temperature between about −50° C. and about 30° C. for about 1 to about 100 hours to form a dantrolene sodium lyophilized preparation.

In another embodiment, lyophilizing the pre-lyophilization solution comprises: i) freezing the pre-lyophilization solution to a temperature below about −40° C. to form a frozen solution; ii) holding the frozen solution at or below −40° C. for at least 2 hours; iii) ramping the frozen solution to a primary drying temperature between about −40° C. and about 30° C. to form a dried solution; iv) holding for about 10 to about 70 hours; v) ramping the dried solution to a secondary drying temperature between about 20° C. and about 40° C.; and vii) holding for about 5 to about 40 hours to form a dantrolene sodium lyophilized preparation.

In another embodiment, the lyophilization cycle includes starting with the pre-lyophilization solution at a shelf temperature for loading of about 0° C. to about 30° C., about 5° C. to about 25° C., about 5° C. to about 15° C.

In another embodiment, the lyophilization cycle includes ending with unloading at about 0° C. to about 30° C., about 5° C. to about 25° C., about 5° C. to about 15° C., in a pharmaceutically acceptable container that is hermetically sealed.

In another embodiment, the lyophilization cycle includes wherein the pressure is about 50 to about 200 microns, about 50 to about 150 microns, about 100 to about 150 microns throughout primary drying and about 50 to about 200 microns, about 50 to about 150 microns, about 100 to about 150 microns throughout secondary drying.

Another embodiment of the invention is the lyophilized powder or preparation obtained from the methods of preparing a dantrolene sodium lyophilized preparation disclosed herein.

The invention also involves dantrolene sodium formulations for lyophilization that include an excipient and a stabilizing concentration of an organic solvent. In one embodiment, the organic solvent further comprises an alkali. In one embodiment, the pre-lyophilization solution comprises about 1 to about 1000 mg/mL excipient. In another embodiment, the pre-lyophilization solution comprises about 1 to about 500 mg/mL excipient. In another embodiment, the pre-lyophilization solution comprises about 10 to about 100 mg/mL excipient. One formulation includes dantrolene sodium at a concentration of about 0.01 to about 15 mg/mL, mannitol at a concentration of about 1 to about 200 mg/mL, tertiary-butyl alcohol at a concentration of about 1% to about 50% (v/v) and water. Another formulation includes dantrolene sodium at a concentration of about 0.05 to about 5 mg/mL, mannitol at a concentration of about 8.0 mg/mL to about 100 mg/mL, tertiary-butyl alcohol at a concentration of about 1% to about 30% (v/v) and water. Included in this embodiment of the invention are the lyophilized preparations made from such dantrolene sodium formulations.

Included in the inventions are methods of treating a medical condition in a patient that involve administering a therapeutically effective amount of a pharmaceutical composition of the invention where the condition is amenable to treatment with the pharmaceutical composition.

Included in the inventions are the use of the pharmaceutical compositions or pharmaceutical preparations of the invention in the manufacture of a medicament for the treatment of a medical condition, as defined herein, in a patient that involve administering a therapeutically effective amount of a pharmaceutical composition of the invention where the condition is amenable to treatment with the pharmaceutical composition.

Also included in the invention are methods of treating in which the pharmaceutical compositions of the invention are in combination with one or more additional therapeutic agents where the additional agent is given prior, concurrently, or subsequent to the administration of the pharmaceutical composition of the invention.

The invention also encompasses a pharmaceutical dosage form of dantrolene wherein the dosage form comprises a vial or other pharmaceutically acceptable container. Preferred concentrations of dantrolene sodium include about 1 to about 500 mg/container, about 5-50 mg/container, about 5 mg to about 20 mg/container and about 10 mg to about 20 mg/container.

The present invention also includes pre-lyophilized pharmaceutical compositions of dantrolene sodium. In one embodiment the pre-lyophilized composition includes dantrolene sodium, mannitol, tertiary-butyl alcohol, sodium hydroxide and water.

In one embodiment, the active pharmaceutical compounds that can be used in the present invention include dantrolene, aminodantrolene, azumolene, and salts and mixtures thereof. In one embodiment, the active pharmaceutical are dantrolene sodium, 3½H$_2$O, azumolene sodium, 2H$_2$O and aminodantrolene sodium.

These methods may employ the compounds of this invention in a monotherapy or in combination one or more additional therapeutic agents. Such combination therapies include administration of the agents in a single dosage form or in multiple dosage forms administered at the same time or at different times.

In another embodiment, the active pharmaceutical compound further comprises at least one additional agent selected from general anesthetics; hypnotic/sedatives/antianxiety drugs; antiepileptics; antipyretic/analgesic/anti-inflammatory agents; analeptic/antihypnotic agents; antiparkinsonian drugs; psychotropic/neurotropic drugs; cns drugs; local anesthetics; skeletal muscle relaxant; autonomic drugs; antispasodics; antivertigo drugs; sense organ drugs; cardiotonics; antiarrhythmic drugs; diuretics; antihypertensive drugs; vasoconstrictors; vasodilators; cardiovascular drugs; respiratory stimulants; antitussives; expectorant's; brochodilators; antidiarrheal drugs/drugs for controlling intestinal function; peptic ulcer remedies; stomachics/digestants; laxatives/clysters; cholagogues; gastrointestinal drugs; thyroid/parathyroid hormone drugs; anabolic steroid drugs; corticoid drugs; male hormone drugs; estrogen/progestin drugs; hormone drugs; urinary tract drugs; oxytocics; vitamins; hemostatics; anticoagulants; liver disease remedies; antidotes; arthrifuges; antidiabetics; metabolism drugs; antitumor drugs; antiallergic agents; antibiotics; sulfa drugs; antituberculosis drugs; antileprotics; synthetic antimicrobial agents; antiviral agents; chemotherapeutic drugs; anthelmintics; and narcotics.

In another embodiment, the active pharmaceutical compound is a hypertonic solution that further contains at least one additional agent selected from adenine nucleosides, nucleotides, amino acids, mannitol, vitamin C, glutathione, vitamin E, magnesium, dantrolene, corticosteroids, promazine, nicholin, 21-amino steroids, non-steroidal anti-inflammatory agents, calcium antagonists, and K-ATP channel openers.

These and other embodiments of the invention are described herein below or are evident to persons of ordinary skill in the art based on the following disclosures.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

This invention, as defined in the claims, can be better understood with reference to the following drawings:

FIG. 1 shows a schematic diagram of the formulation procedure for cooling and addition of co-solvent. The diagram is a pictorial representation of the formulation procedure for the preparation of the rapidly reconstituted freeze-dried DS-IV product using a TBA-aqueous co-solvent system. Mixing and Cooling is accomplished as follows: To an aqueous (WFI) solution of mannitol containing enough of NaOH to bring the pH to 10.1-10.3 at 50° C., DS (API) is added. Mixing at 50° C. continues for 20 minutes. This is followed by a period of cooling down to 25° C. when TBA is added.

In the following description of the illustrated embodiments, references are made to the accompanying drawings, which form a part hereof, and in which is shown by way of illustration various embodiments in which the invention may be practiced. It is to be understood that other embodiments may be utilized and structural and functional changes may be made without departing from the scope of the present invention.

DETAILED DESCRIPTION OF THE INVENTION

Before the present methods and compositions are described, it is to be understood that this invention is not limited to the specific methodology, devices, formulations, and compositions described as such may, of course, vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "and", and "the" include plural referents unless the context clearly dictates otherwise.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All references, publications, patents, patent applications, and commercial materials mentioned herein are incorporated herein by reference for all purposes including for describing and disclosing the cell lines, vectors, and methodologies which are reported in the publications which might be used in connection with the invention. Nothing herein is to be construed as an admission that the invention is not entitled to antedate such disclosure by virtue of prior invention.

In order to provide a clear and consistent understanding of the specification and claims, including the scope to be given such terms, the following definitions are provided:

The specification contains the following abbreviations: Active Pharmaceutical Ingredient (API), Dantrolene Sodium (DS), Dantrolene Sodium Intravenous (DS-IV), Generally Regarded as Safe (GRAS), Potassium Hydroxide (KOH), Malignant Hyperthermia (MH), Sodium Hydroxide (NaOH), Tertiary Butyl Alcohol, t-butanol, tertiary butanol, or tert-butyl alcohol (TBA), and United States Pharmacopeia (USP).

The term "administration" of the pharmaceutically active compounds and the pharmaceutical compositions defined herein includes systemic use, as by injection (especially parenterally), intravenous infusion, suppositories and oral administration thereof, as well as topical application of the compounds and compositions. Intravenous administration is particularly preferred in the present invention.

"Ameliorate" or "amelioration" means a lessening of the detrimental effect or severity of the disease in the subject receiving therapy, the severity of the response being determined by means that are well known in the art.

By "compatible" herein is meant that the components of the compositions which comprise the present invention are capable of being commingled without interacting in a manner which would substantially decrease the efficacy of the pharmaceutically active compound under ordinary use conditions.

The terms "effective amount" or "pharmaceutically effective amount" refer to a nontoxic but sufficient amount of the agent to provide the desired biological result. That result can be reduction and/or alleviation of the signs, symptoms, or causes of a disease, such as neural diseases and malignant hyperthermia, or any other desired alteration of a biological system. Such amounts are described below. An appropriate "effective" amount in any individual case may be determined by one of ordinary skill in the art using routine experimentation.

As used herein, the term "excipient" means the substances used to formulate active pharmaceutical ingredients (API) into pharmaceutical formulations; in a preferred embodiment, an excipient does not lower or interfere with the primary therapeutic effect of the API. Preferably, an excipient is therapeutically inert. The term "excipient" encompasses carriers, diluents, vehicles, solubilizers, stabilizers, bulking agents, acidic or basic pH-adjusting agents and binders. Excipients can also be those substances present in a pharmaceutical formulation as an indirect or unintended result of the manufacturing process. Preferably, excipients are approved for or considered to be safe for human and animal administration, i.e., GRAS substances (generally regarded as safe). GRAS substances are listed by the Food and Drug administration in the Code of Federal Regulations (CFR) at 21 CFR 182 and 21 CFR 184, incorporated herein by reference. In one embodiment, the excipients include, but are not limited to, hexitols, including mannitol and the like as well as sodium or potassium hydroxides (NaOH or KOH) and mixtures thereof.

As used herein, the terms "formulate" refers to the preparation of a drug, e.g., dantrolene, in a form suitable for administration to a mammalian patient, preferably a human. Thus, "formulation" can include the addition of pharmaceutically acceptable excipients, diluents, or carriers and pH adjusting agents.

As used herein, the term "lyophilized powder" or "lyophilized preparation" refers to any solid material obtained by lyophilization, i.e., freeze-drying of an aqueous solution. The aqueous solution may contain a non-aqueous solvent, i.e. a solution composed of aqueous and one or more non-aqueous solvent(s). In one embodiment, a lyophilized preparation is one in which the solid material is obtained by freeze-drying a solution composed of aqueous and one or more non-aqueous solvents. In one embodiment, the non-aqueous solvent is an alcohol. In one specific embodiment, the non-aqueous solvent comprises at least butanol. In one specific embodiment, the non-aqueous solvent comprises at least tert-butyl alcohol.

The term "organic solvent" means an organic material, usually a liquid, capable of dissolving other substances. As used herein, "trace amount of an organic solvent" means an amount of solvent that is equal to or below recommended levels for pharmaceutical products, for example, as recommended by ICH guidelines (International Conferences on Harmonization, Impurities—Guidelines for Residual Solvents. Q3C. Federal Register. 1997; 62(247):67377). The lower limit is the lowest amount that can be detected.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

As used herein, a "pharmaceutically acceptable carrier" is a material that is nontoxic and generally inert and does not affect the functionality of the active ingredients adversely. Examples of pharmaceutically acceptable carriers are well known and they are sometimes referred to as dilutents, vehicles or excipients. The carriers may be organic or inorganic in nature. Examples of pharmaceutically acceptable carriers that may be present in the present lyophilized formulations may be gelatin, lactose, starch, cocoa butter, dextrose, sucrose, sorbitol, mannitol, gum acacia, alginates, cellulose, talc, magnesium stearate, polyoxyethylene sorbitan monolaurate, polyvinylpyro-lidone (PVP) and other commonly used pharmaceutical carriers. In one embodiment, the pharmaceutical carrier comprises mannitol. In addition, the formulation may contain minor amounts of pH adjusting agents such as sodium hydroxide (NaOH) additives such as flavoring agents, coloring agents, thickening or gelling agents, emulsifiers, wetting agents, buffers, stabilizers, and preservatives such as antioxidants.

By "physiological pH" or a "pH in the physiological range" is meant a pH in the range of approximately 7.2 to 8.0 inclusive, more typically in the range of approximately 7.2 to 7.6 inclusive.

The term "pharmaceutical composition" as used herein shall mean a composition that is made under conditions such that it is suitable for administration to humans, e.g., it is made under GMP conditions and contains pharmaceutically acceptable excipients, e.g., without limitation, stabilizers, pH adjusting agents such as NaOH, bulking agents, buffers, carriers, diluents, vehicles, solubilizers, and binders. As used herein pharmaceutical composition includes but is not limited to a pre-lyophilization solution or dispersion as well as a liquid form ready for injection or infusion after reconstitution of a lyophilized preparation.

A "pharmaceutical dosage form" as used herein means the pharmaceutical compositions disclosed herein being in a container and in an amount suitable for reconstitution and administration of one or more doses, typically about 1-2, 1-3, 1-4, 1-5, 1-6, 1-10, or about 1-20 doses. Preferably, a "pharmaceutical dosage form" as used herein means a lyophilized pharmaceutical composition disclosed herein in a container and in an amount suitable for reconstitution and delivery of one or more doses, typically about 1-2, 1-3, 1-4, 1-5, 1-10, 1-20, or about 1-30 doses. The pharmaceutical dosage form can comprise a vial or syringe or other suitable pharmaceutically acceptable container. The pharmaceutical dosage form suitable for injection or infusion use can include sterile aqueous solutions or dispersions or sterile powders comprising an active ingredient which are adapted for the extemporaneous preparation of sterile injectable or infusible solutions or dispersions. In all cases, the ultimate dosage form should be sterile, free of endotoxins and particulates, within the USP requirements, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The prevention of the growth of microorganisms can be accomplished by various antibacterial and antifungal agents, for example, parabens, chlorobutanol, phenol, sorbic acid, thimerosal, and the like.

By "stable pharmaceutical composition" is meant any pharmaceutical composition having sufficient stability to have utility as a pharmaceutical product. The shelf-life or expiration can be that amount of time where the active ingredient degrades to a point below 90% purity. For purposes of the present invention stable pharmaceutical composition includes reference to pharmaceutical compositions with specific ranges of impurities as described herein.

As used herein, the term "subject" encompasses mammals and non-mammals. Examples of mammals include, but are not limited to, any member of the Mammalia class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or sex.

As used herein, the terms "treating" or "treatment" of a disease include preventing the disease, i.e. preventing clinical symptoms of the disease in a subject that may be exposed to, or predisposed to, the disease, but does not yet experience or display symptoms of the disease; inhibiting the disease, i.e., arresting the development of the disease or its clinical symptoms, such as by suppressing hyperthermia; or relieving the disease, i.e., causing regression of the disease or its clinical symptoms.

As used herein, the term "vial" refers to any walled container, whether rigid or flexible.

General

The invention provides for stable, pharmaceutically acceptable compositions prepared from an active pharmaceutical agent. In particular, the invention provides formulations for the lyophilization of active pharmaceutical agents with low solubility upon reconstitution with physiological buffer or saline. The lyophilized powder obtained from the formulations made by the present invention is more easily reconstituted.

The invention also provides for stable, pharmaceutically acceptable compositions prepared from dantrolene. In particular, the invention provides formulations for the lyophilization of dantrolene sodium. The lyophilized powder obtained from such formulations is more easily reconstituted than the presently available lyophilized powder of dantrolene.

In one embodiment, the active pharmaceutical compounds that can be used in the present invention include dantrolene, aminodantrolene, azumolene, and salts and mixtures thereof. In one embodiment, the active pharmaceutical compounds are dantrolene sodium, $3\frac{1}{2}H_2O$, azumolene sodium, $2H_2O$ and aminodantrolene sodium.

The present invention further provides formulations of dantrolene useful for treating various disease states, especially neural diseases and malignant hyperthermia. The formulations described herein can be administered alone or in combination with at least one additional therapeutic agent.

Another aspect of the invention is conditions and means for enhancing the solubility of dantrolene sodium during the lyophilization reconstitution process.

As described herein, a lyophilized formulation of dantrolene sodium is achieved following removal of an organic solvent in water. The most typical example of the solvent used to prepare this formulation is alcohol. In one embodiment, the alcohol is butanol. In another embodiment, the alcohol is tertiary butanol (TBA). Other organic solvents can be used including ethanol, n-propanol, n-butanol, isoproponal, ethyl acetate, dimethyl carbonate, acetonitrile, dichloromethane, methyl ethyl ketone, methyl isobutyl ketone, acetone, 1-pentanol, methyl acetate, methanol, carbon tetrachloride, dimethyl sulfoxide, hexafluoroacetone, chlorobutanol, dimethyl sulfone, acetic acid, cyclohexane. These preceding solvents may be used individually or in combination. Useful solvents must form stable solutions with dantrolene sodium and must not react chemically or appreciably degrade or deactivate the API. The solubility of dantrolene sodium in the selected solvent must be high enough to form commercially useful concentrations of the drug in solvent. Additionally, the solvent should be capable of being removed easily from an aqueous dispersion or solution of the drug product, e.g., through lyophilization or vacuum drying. In one embodiment, a solution having a concentration of about 1-80 mg/mL is used; in another embodiment, a solution of about 0.05 to 10 mg/mL is used, in another embodiment, a solution of about 0.1 to about 3.5 mg/mL is used.

A pharmaceutically acceptable lyophilization excipient can be dissolved in the aqueous phase during the formulation process. Examples of excipients useful for the present invention include, without limitation, sodium or potassium phosphate, citric acid, tartaric acid, gelatin, glycine, and carbohydrates such as lactose, sucrose, maltose, glycerin, dextrose, dextran, trehalose and hetastarch. Mannitol is a preferred excipient. Other excipients that may be used if desired include antioxidants, such as, without limitation, ascorbic acid, acetylcysteine, cysteine, sodium hydrogen sulfite, butyl-hydroxyanisole, butyl-hydroxytoluene or alpha-tocopherol acetate, or chelators and pH adjusting agents.

A typical formulation and lyophilization cycle useful in accordance with the present invention is provided below. Lyophilization can be carried out using standard equipment as used for lyophilization or vacuum drying. The cycle may be varied depending upon the equipment and facilities used for the fill/finish.

In accordance with a typical embodiment of the present invention, an aqueous pre-lyophilization solution or dispersion is first formulated in a pharmaceutically acceptable compounding vessel. The solution is aseptically filtered into a sterile container, filled into an appropriate sized vial, partially stoppered and loaded into the lyophilizer.

In one embodiment, using lyophilization techniques described herein, the solution is lyophilized until moisture content in the range of about 0.01 to about 8.0 percent is achieved. The resulting lyophilization powder can be readily reconstituted with Sterile Water for Injection, or other suitable carrier, to provide liquid formulations of dantrolene sodium, suitable for internal administration e.g., by parenteral injection. For intravenous administration, the reconstituted liquid formulation, i.e., the pharmaceutical composition, is preferably a solution.

In one embodiment, the method for lyophilizing the pre-lyophilization solution comprises:
i) cooling the pre-lyophilization solution to a temperature below about −30° C., preferably below about −40° C., to form a frozen solution;
ii) holding the frozen solution at or below −30° C., preferably at or below −40° C., more preferably at or below −50° C., for at least 1 hour, preferably for at least 2 hours; more preferably for 2-4 hours;
iii) ramping the frozen solution to a primary drying temperature between about −45° C. and about 20° C. to form a dried solution, wherein the ramping occurs over a period of at least 1 hour, preferably for at least 2 hours; more preferably for 2-3 hours;
iv) holding at a temperature of about 20° C. for about 10 to about 70 hours; preferably 20 to about 50 hours; more preferably about 30 to about 40 hours; most preferably from about 30 hours to about 35 hours;
v) ramping the dried solution to a secondary drying temperature between about 25° C. and about 50° C., preferably at least 30° C., more preferably at least 35° C., most preferably at least 40° C., wherein the ramping occurs over a period of at least 30 minutes, preferably for at least 1 hour; more preferably for 1-2 hours; and
vi) holding at the secondary drying temperature for about 1 to about 30 hours; preferably 2 to about 20 hours; more preferably about 3 to about 10 hours; most preferably from about 5 hours to about 7 hours; to form a dantrolene sodium lyophilized preparation.

In another embodiment, the method for lyophilizing the pre-lyophilization solution further comprises the steps:
vii) ramping the dried solution to a temperature between about 25° C. and about 40° C., preferably less than 35° C., more preferably less than 30° C., wherein the ramping occurs over a period of at least 30 minutes, preferably for at least 1 hour; more preferably for 1-2 hours; and
viii) holding at the new temperature for at least 1 hour, preferably for at least 2 hours, more preferably for 2-4 hours; to form a dantrolene sodium lyophilized preparation.

In one embodiment of the invention, the pressure is about 70 to about 130 microns throughout primary drying cycle, preferably the pressure is about 80 to about 120 microns throughout primary drying and more preferably from about 90 to about 110 microns throughout primary drying. In another embodiment of the invention, the pressure is about 90 to about 150 microns throughout secondary drying cycle, preferably the pressure is about 100 to about 140 microns throughout secondary drying and more preferably from about 110 to about 130 microns throughout secondary drying.

In another embodiment, the method for lyophilizing the pre-lyophilization solution comprises:
i) starting with a shelf temperature of about 25° C. for loading;
ii) freezing to about −40 to −50° C. over about 2-4 hours;
iii) holding at −45° C. for about 2-3 hours;
iv) ramping to about 20° C. over about 2-3 hours;
v) holding at about 20° C. for 30-35 hours;
vi) ramping to about 40° C. over about 1-2 hour;
vii) holding at about 40° C. for about 5-7 hours;
vii) ramping to about 30° C. over about 1-2 hours; and
ix) holding at about 30° C. for about 2-4 hrs;
to form a dantrolene sodium lyophilized preparation.

In one embodiment, the pre-lyophilization solution has a starting temperature above about 5° C., preferably above 15° C., to facilitate loading. In another embodiment, the pre-lyophilization solution is frozen at a temperature of about −40° C. to about −50° C., to form a frozen solution.

In another embodiment, the pre-lyophilization solution or dispersion normally is first formulated in a pharmaceutically acceptable container by: 1) adding an excipient, such as mannitol (about 0 to about 500 mg/mL) with mixing to water at ambient temperature, 2) adding an organic solvent (0.5-99.9% v/v), such as TBA to the aqueous solution with mixing at about 20-35° C., 4) adding dantrolene sodium to the desired concentration with mixing, 5) adding water to achieve the final volume, and 6) cooling the solution to a temperature of from about 10° C. to about 30° C., preferably about 25° C. In one embodiment, the excipient may be added during a later step such as after adding the organic solvent. Although the preceding steps are shown in a certain order, it is understood that one skilled in the art can change the order of the steps and quantities as needed. Quantities can be prepared on a weight basis also.

In another embodiment, the pre-lyophilization solution or dispersion normally is first formulated in a pharmaceutically acceptable container by: 1) adding an excipient, such as mannitol (about 0 to about 500 mg/mL) with mixing with sterile water at ambient temperature and enough sodium hydroxide (NaOH) in 100% sterile water to bring the pH to 10.1 to 10.3° C., 2) adding dantrolene sodium to the desired concentration with mixing, 3) adding sterile water to achieve the final volume, 4) heating the solution to about 40° C. to about 70° C., preferably about 45° C. to about 60° C., more preferably about 50° C. for a time sufficient to substantially solubilize the dantrolene sodium, 5) cooling the solution to about 10° C. to about 35° C., preferably to a temperature about 30° C., more preferably to a temperature less than about 30° C., more preferably to a temperature less than about 26° C., adding an organic solvent (0.5-99.9% v/v), such as TBA to the aqueous solution with mixing at about 20-35° C., and 6) cooling the solution to about 10° C. to about 30° C., preferably about 5° C. In one embodiment, the excipient may be added during a later step such as after cooling the solution in step 5) or after adding the organic solvent. Although the preceding steps are shown in a certain order, it is understood that one skilled in the art can change the order of the steps and quantities as needed. Quantities can be prepared on a weight basis also.

The pre-lyophilization solution or dispersion can be sterilized prior to lyophilization, sterilization is generally per-formed by aseptic filtration, e.g., through a 0.22 micron or less filter. Multiple sterilization filters can be used. Additional sterilization of the solution or dispersion can be achieved by other methods known in the art, e.g., radiation.

In this case, after sterilization, the solution or dispersion is ready for lyophilization. Generally, the filtered solution will be introduced into a sterile receiving vessel, and then transferred to any suitable container or containers in which the formulation may be effectively lyophilized. Usually the formulation is effectively and efficiently lyophilized in the containers in which the product is to be marketed, such as, without limitation, a vial, as described herein and as known in the art.

A typical procedure for use in lyophilizing the pre-lyophilization solutions or dispersions is set forth below. However, a person skilled in the art would understand that modifications to the procedure or process may be made depending on such things as, but not limited to, the pre-lyophilization solution or dispersion and lyophilization equipment.

Initially, the product is placed in a lyophilization chamber under a range of temperatures and then subjected to temperatures well below the product's freezing point, generally for several hours. In one embodiment, the product is chilled below the freezing point of the solution preferably to about −5° C., more preferably to about −10° C. or lower, even more preferably to about −20° C. or lower. In one embodiment, the temperature will be at or below about −40° C. for at least 2 hours. After freezing is complete, the chamber and the condenser are evacuated through vacuum pumps, the condenser surface having been previously chilled by circulating refrigerant. Preferably, the condenser will have been chilled below the freezing point of the solution preferably to about −40° C. In another embodiment, the condenser will have been chilled to about −45° C. or lower, in another embodiment to about −60° C. or lower. Additionally, evacuation of the chamber should continue until a pressure of about 10 to about 600 mTorr, preferably about 50 to about 150 mTorr is obtained.

The product composition is then warmed under vacuum in the chamber and condenser. This usually will be carried out by warming the shelves within the lyophilizer on which the product rests during the lyophilization process at a pressure ranging from about 10 to about 600 mTorr. The warming process will optimally take place very gradually. In one embodiment, the warming process will take place over the course of several hours. In one embodiment, the product temperature is initially increased from about −40° C. to about 20° C. and maintained for about 10-70 hours. In another embodiment, the product temperature is initially increased from about −46° C. to about 20° C. and maintained for about 20-40 hours.

Additionally, the product temperature can be increased to a temperature to about 25° C.-40° C. over a period of 0-20 hours.

To prevent powder ejection of the lyophilisate from vials, complete removal of the organic solvent and water should be done during the initial drying phase. Complete drying can be confirmed by stabilization of vacuum, condenser temperature and product shelf temperature. After the initial drying, the product temperature should be increased to about 25° C.-40° C. and maintained for about 5-40 hours.

Once the drying cycle is completed, the pressure in the chamber can be slowly released to atmospheric pressure (or slightly below) with sterile, dry-nitrogen gas (or equivalent gas). If the product composition has been lyophilized in containers such as vials, the vials can be stoppered, removed and sealed. Several representative samples can be removed for purposes of performing various physical, chemical, and microbiological tests to analyze the quality of the product.

The lyophilized dantrolene formulation is typically marketed in pharmaceutical dosage form. The pharmaceutical dosage form of the present invention, although typically in the form of a vial, may be any suitable container, such as ampoules, syringes, co-vials, which are capable of maintaining a sterile environment. Such containers can be glass or plastic, provided that the material does not interact with the dantrolene formulation. The closure is typically a stopper, most typically a sterile rubber stopper, preferably a bromobutyl rubber stopper, which affords a hermetic seal.

After lyophilization, the dantrolene lyophilization powder may be filled into containers, such as vials, or alternatively the pre-lyophilization solution can be filled into such vials and lyophilized therein, resulting in vials which directly contain the lyophilized dantrolene formulation. Such vials are, after filling or lyophilization of the solution therein, sealed, as with a stopper, to provide a sealed, sterile, pharmaceutical dosage form. Typically, a vial will contain a lyophilized powder including about 10-500 mg/vial, preferably about 100 mg/vial, dantrolene sodium and about 5 mg-3.0 g/vial, preferably about 3.0 g/vial, mannitol. In another embodiment, the amount of dantrolene sodium is about 5 to about 100 mg/container, about 5-50 mg/vial, about 10 mg to about 30 mg/vial and about 10 mg to about 20 mg/vial.

The lyophilized formulations of the present invention may be reconstituted with water, preferably Sterile Water for Injection, or other substantially sterile fluid such as co-solvents, to provide an appropriate solution of dantrolene sodium for intravenous administration.

The results shown in Table 1 indicate that dantrolene sodium solubility is dependant on temperature and the amount of alcohol in aqueous solutions. For the alcohols tested, the solubility of dantrolene sodium increased as the concentration of alcohol increased. The formation of a precipitant was also dependent on the temperature and time.

Alcohols varied in their effect on solubility. Without wishing to be bound to any particular theory, smaller alcohols such as methanol and ethanol have less of an effect on solubility as compared with larger alcohols (tertiary-butanol and n-butanol). However, the shape of the alcohol is also important. For example tert-butanol was found to be better than iso-butanol in preventing precipitation in this system. The alcohol with the greatest effect on solubility was tertiary-butanol.

The pharmaceutical compositions of the present invention comprise specifically defined dantrolene compounds, used in a safe and effective amount, together with a pharmaceutically acceptable carrier.

The dantrolene compounds used in the compositions of the present invention are those having the following structural formulae:

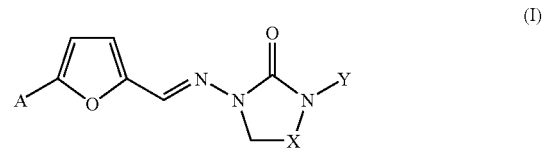

(I)

wherein
A is a member of the group consisting of furyl

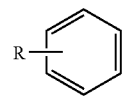

in which R is from one to two substitutes selected from the group consisting of nitro, cyano, amino, chloro, bromo, acetyl, cargboxy, methyl, trifluorimethyl, and hydrogen;

X is a member of the group consisting of carbonyl and methylene; and

Y is a member of the group consisting of hydroxyethyl, butyl, hydrogen, and r-pyridylethyl.

In certain embodiments, the active compound is one or more of the following compounds:

1-[5-(p-nitrophenyl)furfurylideneamino]hydantoin;
1-[5-(p-aminophenyl)furfurylideneamino]hydantoin;
1-[5-(m-nitrophenyl)furfurylideneamino]hydantoin;
1-[5-(p-chlorophenyl)furfurylideneamino]hydantoin;
1-[5-(2,4-dichlorophenyl)furfurylideneamino]hydantoin;
1-[5-(2,methyl-4-nitrophenyl)furfurylideneamino]hydantoin;
1-[5-(p-nitrophenyl)furfurylideneaminio]-2-imidazolidinone;
1-[5-(p-cyanophenyl)furfurylideneamino]hydantoin;
and pharmaceutically acceptable salts thereof.

The active pharmaceutical ingredient (API) dantrolene sodium (DS) (USP) is a hemiheptahydrate salt; 1-[5-(4-nitrophenyl)furfurylidene amino]imidazolidine-2,4-dione, containing 14.5-17.0% of water (3½ moles) and has a molecular weight of 399. The anhydrous salt has a molecular weight of 336.

Dantrolene sodium (USP) is an orange, odorless powder with a melting point of 279-280° C. It is completely soluble in propylene glycol, slightly soluble in ethanol and methanol, and is insoluble in $H_2O$ (15 mg/L). Higher solubility in water at pH 8.0 or greater is exhibited by dantrolene sodium. Its free acid form (dantrolene) is totally insoluble (mg/L), and it is a weak acid with a pKa of about 7.5. However, the extremely low solubility of the free acid prevents an accurate determination of its pKa. The FDA approved lyophilized dantrolene sodium for intravenous injection (DS-IV) product (USP 2007) contains 20 mg of hydrated DS (API)(16.8 mg on the anhydrous basis), 3.0 grams of mannitol and enough NaOH to achieve a pH=9.5 (approximately) upon reconstitution with 60 mL of water for injection. The reconstituted product is administered as a rapid infusion to patients exhibiting the life-threatening condition of thermal hyperthermia during surgery.

Dantrolene sodium has a formula of Formula II:

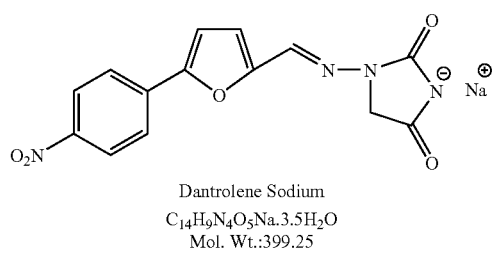

Dantrolene Sodium
$C_{14}H_9N_4O_5Na \cdot 3.5H_2O$
Mol. Wt.:399.25

Dantrolene is an antagonist of the type 3 ryanodine receptor and is commonly given as the sodium salt (sodium dantrium), which is hydrated 1-[[[5-(4-nitrophenyl)2-furanyl]methylene]amino]-2,4-imidazolidinedione sodium salt. Dantrolene is prescribed in the treatment of clinical spasticity resulting from upper motor neuron disorders such as spinal chord injury, cerebral palsy, stroke, or multiple sclerosis. Dantrolene is also effective in reversing the hypermetabolic process of malignant hyperthermia, a genetic disorder of skeletal muscle that is triggered by exposure to anesthetics and certain relaxants.

Other therapeutic uses for dantrolene are known in the art. For example, Dreyer, U.S. Pat. No. 5,597,809, teaches the use of NMDA-receptor antagonists, and also dantrolene, for the treatment of optic neuritis. U.S. Pat. No. 5,506,231 to Lipton teaches the use of dantrolene for the treatment of three conditions specifically associated with AIDS: dementia, myelopathy, and blindness. Dantrolene has been used clinically to treat malignant hypothermia, as it is known to reduce cellular energy requirements, creating a hypothermic environment. Kiyoshi (Patent Abstracts of Japan (1994), publication number 06263636) discloses the use of dantrolene for treatment of cerebral nerve diseases such as geriatric dementia, Parkinson's disease and Huntington's disease.

Non-therapeutic uses for dantrolene include cryopreservation of blood vessels. See U.S. Pat. Nos. 5,158,867; 5,149,621; 5,145,769 and 5,122,110, incorporated herein in their entirety.

Tertiary butyl alcohol (TBA) possesses favorable properties to be utilized in aqueous co-solvent systems for the freeze-drying of pharmaceutical products. The favorable physical properties of TBA include its high vapor pressure, low melting point (freezes completely in most freeze dryers with low expenditure of energy) and readily sublimes (increases sublimation rates) during the primary drying stage of the freeze-drying process. Added to these desirable physical properties, TBA possesses low toxicity as an organic solvent (permissible residual limit about the same as ethyl alcohol, i.e. <5,000 ppm).

TABLE 2

Physicochemical properties of TBA

| Property | Value |
|---|---|
| Formula: | C4H10O |
| Glass Transition | −93° C. |
| Melting Point | 25° C. |
| Boiling Point | 84.6 ± 8.0° C. |
| Density | 0.804 ± 0.06 g/cm3 |
| Enthalpy of Vaporization | 37.89 ± 6.0 kJ/mol |
| Molecular Weight | 74.12 |
| pKa | 15.37 ± 0.29 |

Without wishing to be bound by theory, the utilization of a TBA-aqueous co-solvent system into the DS-IV formulation appears to lead to the following beneficial results:

i. It substantially reduces the freezing time of the "fill solution" (solution that is introduced into the vials) of the formulation.

ii. It causes an approximate two-fold decrease in the drying time of the freeze-dried cake of the DS-IV product in the course of its production.

iii. It substantially reduces the reconstitution time of the freeze-dried (lyophilized) DS-IV product from minutes to less than 60, 50, 40, 30, 20, 10 or fewer seconds. This provides a significant improvement in the pharmacotherapy of patients exhibiting the life-threatening condition of malignant hyperthermia during surgery.

EXAMPLES

The following Examples are provided to illustrate certain aspects of the present invention and to aid those of skill in the art in practicing the invention. These Examples are in no way to be considered to limit the scope of the invention in any manner.

Example 1

Formulation of DS-IV Product

In one embodiment, the DS-IV product is a lyophilized (freeze-dried) powder containing approximately 16.8 mg of anhydrous dantrolene sodium (API) (DS) (equivalent to 20 mg of hydrous DS (API) containing 14.5% to 18% of moisture), 3 g of mannitol and enough NaOH to achieve a pH value of approximately 8.8 to 10.9 upon reconstitution with 60 mL of water for injection (WFI) per vial.

Without wishing to be bound by theory, it is believed that due to the fact that DS (API) is highly insoluble, it must be dissolved at an alkaline environment (above its pKa 7.4 value). Since DS is susceptible to an alkaline hydrolysis, it must be dissolved as rapidly as possible during its formulation step. To achieve a rapid dissolution of DS, higher temperatures have to be utilized. The alkalinity (pH value), temperature and duration of heating of the liquid DS formulation play a role in the strength (percent of API) of the final lyophilized DS-IV product. The conditions may be appropriately adjusted to achieve a favorable strength (94-97%) in the final product.

It is known that an aqueous co-solvent system may be used to facilitate the dissolution of an insoluble drug. When an aqueous co-solvent system consisting of 5%, 10% and 20% TBA was used in the DS formulation, the drug (DS) (API) remained unsolubilized even after 90 minutes of mixing time at room temperature. Surprisingly, the addition of TBA to the aqueous portion of the DS formulation did not increase the solubilization rate of DS (API) as is the case with the majority of drug formulations in which the TBA-aqueous co-solvent system is used. However, it was discovered that the use of the TBA shortened the freezing time of the pre-lyophilized "fill" solution, the freeze-drying time and the reconstitution time of the freeze-dried cake of the DS-IV product.

FIG. 1 shows the preferred manner by which solubilization of DS is achieved if the API (DS) is first mixed with its formulation constituents (e.g., about 3 g of mannitol and enough of NaOH in 100% sterile water to bring the pH to about 8.8 to about 11, preferably, from about 10 to about 10.5, more preferably from about 10.1 to about 10.3) at about 50° for a period of about 20 minutes.

This is followed by a period of cooling (about 45-60 min) down to about 25° C. The TBA is subsequently added at about 25° C. (See FIG. 1) to complete the formulation process. Importantly, the addition of TBA at about 25° C. does not cause any undesirable loss of the strength (percent of API) of the formulation. This is substantiated by the fact that when the TBA-treated formulation was freeze-dried, the final reconstituted product of DS-IV exhibited strength of 95±1% (See Table 3).

TABLE 3

Summary of percent (%) assay of DS-IV vials

| TBA % | Assay % |
|---|---|
| 0 | 95.94 ± 0.54 |
| 5 | 96.40 ± 0.60 |
| 10 | 94.66 ± 0.24 |
| 20 | 96.22 ± 0.70 |

The Impact of TBA on the Freeze-Drying Process of DS-IV Formulation

In general, the presence of TBA solvent affects the freezing characteristics of a solution. Furthermore, it significantly impacts the crystal morphology of the ice, the drying rates, the surface area of the dried cake and reconstitution times of lyophilisates (freeze-dried cake) [2].

The size and shape of the ice crystals depend on the nature and quantity of the organic solvents used in co-solvent system. Thermal analysis studies have been used to evaluate the various stable and metastable states which form with TBA-water systems during freezing. Adding TBA at different ratios was found to cause the formation of large needle-shaped ice crystals, which when sublimed they created a more porous and less resistant matrix which facilitated the drying process. Thus, drying times can be decreased by approximately 30-50% [3].

Impact of TBA on Sublimation Rates

Improvements in the rate of mass transfer of a solvent through a partially dried cake layer increases the sublimation rate and hence it decreases the time for the primary drying phase of the freeze-dry cycle. This leads in the overall reduction of the freeze-drying process which translates in considerable savings in energy and cost of product manufacturing.

Reduction in Drying Time and Freezing Time of DS-IV Product Cake

The present invention reveals that the introduction of about 2% to about 20% TBA into the DS-IV formulation results in an approximate two-fold reduction in drying time of its lyophilisate. The increased drying rate is probably caused by the formation of needle-shaped ice crystals which create a porous structure, which in turn facilitate the mass transfer of water vapor due to decreased cake resistance and the increase in its surface area.

A typical example of freeze-drying cycle of DS-IV product, produced with about 5% TBA aqueous co-solvent system, comprises of the following segments: 1) starting with a shelf temperature of about 25° C. for loading; 2) freezing to about −40 to −50° C. over about 2-4 hours; 3) holding at −45° C. for about 2-3 hours; 4) ramping to about 20° C. over about 2-3 hours; 5) holding at about 20° C. for 30-35 hours; 6) ramping to about 40° C. over about 1-2 hour; 7) holding at about 40° C. for about 5-7 hours; 8) ramping to about 30° C. over about 1-2 hours; 9) holding at about 30° C. for about 2-4 hrs. The pressure is about 90-110 microns throughout primary drying and 110-130 microns throughout secondary drying.

Compared to the original freeze drying cycle (with no TBA), the addition of TBA in the DS-IV formulation, has reduced the total freeze-drying cycle duration by 33% (i.e., from 75 hours to about 50 hours or less).

Enhancement in the Reconstitution Time of the Lyophilized DS-IV Product by TBA

Due to the increased porous structure of the DS-IV lyophilized product which was created by the introduction of TBA, the reconstitution time of the DS-IV product was decreased from 1 to 3 minutes per vial to less than 10 seconds (See Table 4). This almost instantaneous reconstitution of the DS-IV lyophilized powder constitutes a significant improvement in the treatment of patients with malignant hyperthermia. The recommended DS dose for treatment of NH ranges from 1 mg/kg to 10 mg/kg. If we consider that each vial containing 0.02 g of DS (API), then the above recommended doses translate to a minimum of four (4) vials to a maximum of 36 vials per MH episode. The Merck Manual (18th edition, 2006) recommends a treatment for MH that starts with 2.5 mg/kg (9-10 vials). It is also recommended that treatment should be initiated immediately after symptoms of NH develop. On the average, patients exhibiting MH require a rapid intravenous (IV) infusion of nine to ten (9-10) (2.5 mg/kg) vials of DS-IV product, each reconstituted with 60 mL of sterile water for injection (WFI). In many cases, the number of DS-IV vials used ranges from 10-20. Cases of NH requiring as many as 36 vials of DS-IV have been recorded. The length of time to reconstitute 10-36 vials (1 to 3 min each required for reconstitution) creates an issue when considering death due to MH can occur in as short time as 30 min from onset. In adult patients, temperatures exceeding 41° C. (105.8° F.) could prove fatal in periods of MH exceeding 30 min (Merck Manual, 18$^{th}$ Edition, 2006).

TABLE 4

Reconstitution times of DS-IV product before and after utilization of the TBA-aqueous co-solvent system

| TBA % | Time (sec) |
| --- | --- |
| 0 | <90 |
| 5 | <10 |
| 10 | <10 |
| 20 | <10 |

It has now been discovered that dantrolene sodium prevents or reduces arrhythmia in hypothermic and normothermic warm-blooded animals. In particular, dantrolene sodium is effective in the treatment of supraventricular tachycardias, in suppressing slow responses in infarcted tissues and in abolishing ventricular premature beats or tachycardias originating in these tissues, and in correcting ventricular rhythm disturbances due to reentry.

In addition, information regarding procedural or other details supplementary to those set forth herein is described in cited references specifically incorporated herein by reference.

It would be obvious to those skilled in the art that modifications or variations may be made to the preferred embodiment described herein without departing from the novel teachings of the present invention. All such modifications and variations are intended to be incorporated herein and within the scope of the claims.

REFERENCES

1. Practical aspects of lyophilization using non-aqueous co-solvent systems. Dirk L. Teagarden, and David S. Baker. Department of Sterile Products Development, Pharmacia Corporation, 7000 Portage Road, Kalamazoo, Mich. 49001-0199, USA
2. The effect of tertiary butyl alcohol on the resistance of the dry product layer during primary drying. Pharmaceutical Research, Kasra Kasraian and Patrick DeLuca. 12 (4), 491-495, 1995
3. Thermal analysis of the tertiary butyl alcohol-water system and its implications on freeze-drying. Pharmaceutical Research, Kasra Kasraian and Patrick DeLuca. 12 (4), 484-490, 1995
4. Freeze-drying of tertiary butanol/water co-solvent systems: a case report on formation of friable freeze-dried powder of tobramycine sulfate. Journal of Pharmaceutical Sciences. Wittaya-Areekul Sackchai et. al. 91(4), 1147-55, 2002

What is claimed is:

1. A stable and lyophilized formulation of an active pharmaceutical compound made by the process comprising a) dissolving the active pharmaceutical compound in an alkaline solution of water and organic co-solvent solution comprising between about 1% to about 99% (v/v) organic co-solvent to form a pre-lyophilization solution; and b) lyophilizing the pre-lyophilization solution to form a powder; where the co-solvent is selected from the group consisting of one or more of tertiary butanol, n-propanol, n-butanol, isopropanol, ethanol, and methanol; where the active pharmaceutical compound has the formula:

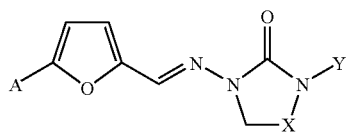

wherein
A has the formula

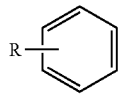

in which R is from one to two substitutes selected from the group consisting of nitro, cyano, amino, chloro, bromo, acetyl, carboxy, methyl, trifluoromethyl, and hydrogen;
X is a member of the group consisting of carbonyl and methylene; and
Y is a member of the group consisting of hydroxyethyl, butyl, hydrogen, and r-pyridylethyl;
wherein step b) comprises:
i) freezing the pre-lyophilization solution to a temperature below about −40° C. to form a frozen solution;
ii) holding the frozen solution at or below −40° C. for at least 2 hours;
iii) ramping the frozen solution to a primary drying temperature between about −40° C. and about 20° C. to form a dried cake;
iv) holding for about 30 to about 70 hours;
v) ramping the dried cake to a secondary drying temperature between about 25° C. and about 40° C.; and
vii) holding for about 5 to about 40 hours to form the stable and lyophilized formulation.

2. The stable and lyophilized formulation of claim 1, wherein the active pharmaceutical compound is selected from the group consisting of:
1-[5-(p-nitrophenyl)furfurylideneamino]hydantoin,
1-[5-(p-aminophenyl)furfurylideneamino]hydantoin,
1-[5-(m-chlorophenyl)furfurylideneamino]hydantoin,
1-[5-(p-chlorophenyl)furfurylideneamino]hydantoin,
1-[5-(2,4-dichlorophenyl)furfurylideneamino]hydantoin,
1-[5-(2-methyl-4-nitrophenyl)furfurylideneamino]hydantoin,
1-[5-(p-nitrophenyl)furfurylideneaminio]-2-imidazolidinone, and
1-[5-(p-cyanophenyl)furfurylideneamino]hydantoin.

3. The stable and lyophilized formulation of claim 1, wherein the active pharmaceutical compound is dantrolene sodium.

4. The stable and lyophilized formulation of claim 3 wherein the residual concentration of organic co-solvent is less than about 0.5%.

5. The stable and lyophilized formulation of claim 3 wherein the concentration of dantrolene sodium degradants in the final lyophilized product is less than about 8%.

6. The stable and lyophilized formulation of claim 3, wherein the formulation is packaged in a vial or other pharmaceutically acceptable container.

7. An injectable formulation of dantrolene sodium formed by reconstituting the lyophilized dantrolene sodium powder of claim 3 with a diluent suitable for intravenous administration.

8. The injectable formulation of claim 7, wherein the injectable formulation comprises about 10 mg to about 30 mg of lyophilized dantrolene sodium powder.

9. The injectable formulation of claim 7, wherein the injectable formulation comprises about 15 mg to about 25 mg of lyophilized dantrolene sodium powder.

10. The stable and lyophilized formulation of claim 3, wherein the organic co-solvent is tertiary butanol.

11. The stable and lyophilized formulation of claim 3, made by a process further comprising the step of adding an excipient and a pH adjusting agent before lyophilization.

12. The stable and lyophilized formulation of claim 11, wherein the excipient comprises mannitol and the pH adjusting agent comprises sodium hydroxide.

13. The stable and lyophilized formulation of claim 12, wherein the pre-lyophilization solution comprises dantrolene sodium at a concentration of about 0.1 to about 5 mg/mL, mannitol at a concentration of about 2 to about 100 mg/mL, tertiary butanol at a concentration of about 1 to about 99% (v/v) and an amount of sodium hydroxide adequate to adjust the pH to a range of from about 9.5 to about 10.5.

14. The stable and lyophilized formulation of claim 12, wherein the pre-lyophilization solution comprises tertiary butanol at a concentration of about 1% to 30%.

15. The stable and lyophilized formulation of claim 3, wherein the formulation is about 96% by weight or greater dantrolene sodium.

16. The stable and lyophilized formulation of claim 3, wherein the formulation can be reconstituted in about 20 seconds or less.

17. The stable and lyophilized formulation of claim 1, wherein step b) results in a freeze-drying cycle of about 54 hours or less.

18. The stable and lyophilized formulation of claim 3, wherein the vial or other pharmaceutically acceptable container contains about 10 to about 500 mg of dantrolene sodium per vial or container.

19. The injectable formulation of claim 7, wherein the injectable formulation is useful for the treatment of malignant hyperthermia.

* * * * *